(12) United States Patent
Jun et al.

(10) Patent No.: US 7,157,404 B1
(45) Date of Patent: Jan. 2, 2007

(54) CATALYST FOR PREPARING HYDROCARBON

(75) Inventors: Ki-Won Jun, Daejeon (KR); Jin-Soo Hwang, Daejeon (KR); Kyu-Wan Lee, Daejeon (KR); Myoung-Jae Choi, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 427 days.

(21) Appl. No.: 10/129,739

(22) PCT Filed: Jul. 14, 2000

(86) PCT No.: PCT/KR00/00766

§ 371 (c)(1),
(2), (4) Date: Aug. 29, 2002

(87) PCT Pub. No.: WO01/34538

PCT Pub. Date: May 17, 2001

(30) Foreign Application Priority Data

Nov. 11, 1999 (KR) .............................. 1999-50014

(51) Int. Cl.
*B01J 23/58* (2006.01)
*B01J 23/72* (2006.01)
*B01J 23/74* (2006.01)
*C07C 27/00* (2006.01)
*C07C 27/06* (2006.01)

(52) U.S. Cl. .................... 502/330; 502/331; 502/332; 502/336; 502/355; 518/713; 518/715; 518/717

(58) Field of Classification Search ........ 502/330–332, 502/336, 355, 415; 518/713, 715, 717
See application file for complete search history.

(56) References Cited

U.S. PATENT DOCUMENTS

| 4,521,394 A | * | 6/1985 | Windawi et al. ............ 423/363 |
| 4,555,526 A | * | 11/1985 | Wakui et al. ............... 518/717 |
| 5,506,273 A | * | 4/1996 | Haruta et al. ............... 518/713 |
| 5,952,540 A |   | 9/1999 | Lee et al. |
| 6,822,008 B1 | * | 11/2004 | Srinivasan et al. ......... 518/717 |
| 2004/0127587 A1 | * | 7/2004 | Espinoza et al. ........... 518/715 |
| 2004/0132834 A1 | * | 7/2004 | Ortego et al. ............... 518/718 |

FOREIGN PATENT DOCUMENTS

| JP | 01-190638 |   | 7/1989 |
| JP | 09087217  | * | 3/1997 |
| JP | 09221437  | * | 8/1997 |

OTHER PUBLICATIONS

Yan, S.R. et al., Promotion effect of Fe-Cu catalyst for the hydrogeneration of $CO_2$ and application to slurry reactor, Appl. Catal., Jan. 1, 2000 194-195, pp. 63-70.

He, D et al., Hydrogenation of CO2 over Cu-Fe-Na/zeolite composite catalysts, Feb. 1, 1998; Chemical Abstracts, vol. 130, No. 25, Jun. 21, 1999, p. 899, col. 1.2, the Abstract 340369s.

* cited by examiner

*Primary Examiner*—David Brunsman
*Assistant Examiner*—Patricia L. Hailey
(74) *Attorney, Agent, or Firm*—Finnegan, Henderson, Farabow, Garrett & Dunner, L.L.P.

(57) ABSTRACT

The present invention relates to a catalyst for preparing hydrocarbons of carbon dioxide and more particularly, the Fe—Cu—K/γ—$Al_2O_3$ catalyst prepared by impregnation which enables producing hydrocarbons in high yield for more than 2000 hours due to its excellent activity and stability.

2 Claims, No Drawings

CATALYST FOR PREPARING HYDROCARBON

BACKGROUND OF THE INVENTION

1. Field of the Invention

The present invention relates to a catalyst for preparing hydrocarbons by hydrogenation of carbon dioxide and more particularly, the Fe—Cu—K/γ—Al$_2$O catalyst prepared by impregnation which enables producing hydrocarbons in high yield for more than 2000 hours due to its excellent activity and stability.

2. Description of Related Art

Carbon dioxide is one of the so-called greenhouse gases. It is known that it absorbs infrared energy and prevents such energy from leaving the atmosphere. Accumulation of carbon dioxide in the atmosphere caused by a huge amount of the fossil and organic-based fuel consumption may therefore contribute to an increase in average global temperatures, resulting in more frequent and more violent natural catastrophes (e.g., periods of drought, flood, storm). However, the world's growing population and increasingly technological society have made it difficult for the world's energy and material resources to keep pace with the current trends. Therefore, increased efforts are required to conserve the environment by restricting the use of fossil and organic-based fuel. To activate this, recycling of carbon dioxide into useful hydrocarbons would help to alleviate the problem of our diminishing hydrocarbon resources.

In order to convert carbon dioxide to useful hydrocarbons, the inventors have disclosed a process for preparing hydrocarbons over a Fe—K/γ—Al$_3$O$_3$ catalyst performed by flowing gas mixture (H$_2$/CO$_2$=1.0~5.0 v/v) into the reactor at 200~500° C., 1~100 atm and 500~20,000 h$^{-1}$ of the space velocity (U.S. Pat. No. 5,952,540). A catalyst used in this process is pretreated Fe—K/γ—Al$_2$O$_3$ by reduction and activation, contains 5~50 wt. % of Fe to total catalyst weight and includes 0.1~1.5 of atomic ratio of K/Fe. However, when Fe—K/γ—Al$_2$O$_3$ catalyst has been used for more than 800 hours, the conversion rate of carbon dioxide to hydrocarbons is decreased by more than 10% and productivity of hydrocarbons is also decreased by more than 20%. On top of that, formation of undesirable carbon monoxide and methane gas are extremely increased by 70% and 30%, respectively.

SUMMARY OF THE INVENTION

In view of the above considerations, the inventors herein have intensively studied to solve deactivation of a catalyst for preparing hydrocarbons out of carbon dioxide by hydrogenation. As a result, the inventors realized that depositions of carbonaceous material such as coke on the surface of the catalyst is a major cause of deactivation of Fe—K/γ—Al$_2$O$_3$ catalyst as disclosed in U.S. Pat. No. 5,952,540 and thus, addition of Cu can provide excellent stability of the catalyst for more than 2000 hours to prepare hydrocarbons by suppressing depositions at carbonaceous on the surface of the catalyst.

Therefore, the object of the present invention is to find a catalyst which not only gives satisfactory activity values but at the same time provides long-term resistance to deactivation by depositions of carbonaceous. Thus, the Fe—K—Cu/γ—Al$_2$O$_3$ catalyst prepared by adding Cu to the conventional Fe—K/γ—Al$_2$O$_3$ catalyst provides that it decreases coke deposits thereon and exhibits sufficient activity, satisfactory yield of hydrocarbons even after using more than 2000 hours and good stability.

DETAILED DESCRIPTION OF THE INVENTION

The catalyst of the present invention used for preparing hydrocarbons by hydrogenation of carbon dioxide is Fe—Cu—K/γ—Al$_2$O$_3$ including 5~50 wt. % of Fe to total catalyst weight and containing 0.07~1 of weight ratio of K/Fe and 0.05~0.5 of weight ratio of Cu/Fe.

A process for preparing hydrocarbons by hydrogenation of carbon dioxide is performed by flowing gas mixture (H$_2$/CO$_2$=1.0~5.0 v/v) into the reactor at 200~500° C., 1~100 atm and 500~20,000 h$^{-1}$ of the space velocity over a catalyst, wherein the catalyst is a pretreated Fe—Cu—K/γ—Al$_2$O$_3$ by reduction and activation, including 5~50 wt. % of Fe to total catalyst weight and containing 0.07~1 of weight ratio of K/Fe and 0.05~0.5 of weight ratio of Cu/Fe.

The detailed description of the present invention is given hereunder.

The present invention relates to the Fe—Cu—K/γ—Al$_2$O$_3$ catalyst which not only gives satisfactory activity values but at the same time provides resistance for more than 2000 hours to deactivation by precipitation of carbonaceous.

The catalyst used in the present invention includes copper (Cu) as well as iron(Fe) and potassium(K) supported on γ-alumina (γ—Al$_2$O$_3$) carrier, wherein a certain amount of copper(Cu) replaced in the active site of iron(Fe) can serve to reduce deposits of carbonaceous and thus, provide excellent activity and stability for long period. A process for preparing the catalyst is as follows.

Aqueous solution of iron-containing salts, potassium-containing salts and copper-containing salts is impregnated into aluminum oxide and mixed. Then the mixture was dried at 80~200° C. for 5~48 hours and calcinated at 400~700° C. for 5~48 hours. A catalyst obtained by the above process becomes mixed state of iron oxide, potassium oxide, copper oxide and aluminum oxide.

Said salts include hydrochloric acid salt, nitric acid salt, sulfuric acid salt, acetic acid salt, oxalic acid salt and various aqueous salts. For example, iron-containing salt is selected from the group consisting of iron chloride, iron nitrate, iron sulfate, iron acetate and iron oxalate. Potassium-containing salt is selected from the group consisting of potassium chloride, potassium carbonate, potassium nitrate and potassium acetate. Copper-containing salt is selected from the group consisting of copper chloride, copper nitrate and copper sulfate.

It is preferred to contain 5~50 wt. % of Fe to total catalyst weight, 0.07~1 of weight ratio of K/Fe and 0.05~0.5 of weight ratio of Cu/Fe, and to use γ—Al$_2$O as a carrier.

According to the present invention to add copper as an activity promoter, if the weight ratio of copper to iron is less than 0.05, it is not sufficient to avoid deactivation by deposits of carbonaceous. If the weight ratio of copper to iron is more than 0.5, the activity of a catalyst becomes extremely poor due to the insufficient iron-surface area as an activity promoter.

Conventional catalysts containing Fe, Cu, K and Al have been reported but the weight ratio of potassium to iron was not more than 0.07 and aluminum oxide was used as a simple carrier without any limitation. However, 0.07~1 of weight ratio of K/Fe increase and use of γ—Al$_2$O$_3$ in the present invention are essential to obtain excellent activity of a catalyst. γ—Al$_2$O$_3$ not only plays a role of a carrier but also increases activity and selectivity of a catalyst through interaction with iron. If the weight ratio of potassium to iron is less than 0.07, it is not proper to activate carbon dioxide to convert to hydrocarbons because alkalinity of a catalyst is not sufficiently increased. In case of using silica which only plays a role of a carrier, activity and selectivity of iron-based catalyst were not increased. Where $\gamma$—$Al_2O_3$ is used, if the content of supported iron is less than 5 wt. %, activity of a catalyst becomes poor and if it is more than 50 wt. %, proper interaction of $\gamma$—$Al_2O_3$ with aluminum oxide cannot be gained.

According to the present invention to obtain sufficient activity, Fe—K—Cu/$\gamma$—$Al_2O_3$ catalyst must be pretreated by reduction and activation. Reduction is performed by flowing hydrogen on Fe—Cu—K/$\gamma$—$Al_2O_3$ at 300~500° C., 1~10 atm and 20~100 ml/g-cat./min of the flow rate, iron oxide reduced changes to iron metal. Activation is performed by flowing the gas mixture ($H_2/CO_2$=0.2~10 v/v) on Fe—Cu—K/$\gamma$—$Al_2O_3$ at 200~400° C., at 10~40 atm and 2~200 ml/g-cat./min of the flow rate and then flowing a gas selected from the group consisting of nitrogen, argon and helium on Fe—Cu—K/$\gamma$—$Al_2O_3$ at 100~400° C., 1~10 atm and 10~100 ml/g-cat./min of the flow rate. Iron of the activated Fe—Cu—K/$\gamma$—$Al_2O_3$ catalyst exists as an appropriate carburized state, and this effectively acts on activating of carbon dioxide.

The reactor for preparing hydrocarbons from carbon dioxide can be a fixed bed reactor, a fluidized bed reactor or a slurry type reactor of liquid phase. The hydrogenation of carbon dioxide is performed under a gas mixture ($H_2/CO_2$=1.0~5.0 v/v) at 200~500° C., 1~100 atm and 500~20,000 $h^{-1}$ of the space velocity. Stoichmetric ratio of the gas mixture ($H_2/CO_2$) is 3~4 v/v. If the condition of hydrogenation is out of this range, the good conversion of carbon dioxide cannot be expected. For example, if the ratio of the gas mixture is less than 1.0 v/v or more than 5.0 v/v, the conversion of carbon dioxide becomes too low. If reaction temperature is lower than 200° C., the conversion rate goes down, and if it is higher than 500° C., the selectivity to $C_{2+}$ hydrocarbons become low because the higher reaction temperature is, the more formation of methane is. If reaction pressure is less than 1 atm, reaction rate is too slow and if it is more than 100 atm, it is difficult to control the reaction. If the space velocity is less than 500 $h^{-1}$, the selectivity is too low and if it is more than 20,000 $h^{-1}$, the conversion is low because the contact time between reactant and catalyst is too short.

Fe—Cu—K/$\gamma$—$Al_2O_3$ catalyst has the best activity from 5 hours to 1,000 hours after the reaction starts. Even though the activity of catalyst is slowly getting decreased after 1000 hours it still provides relatively stable activity due to small different between the conversion amount and the formation amount of hydrocarbons.

According to the above description Fe—Cu—K/$\gamma$—$Al_2O_3$ catalyst pretreated by reduction and activation process is used to generate hydrocarbons from carbon dioxide by hydrogenation for more than 2000 hours in much higher yield and conversion rates than those of processes over conventional catalysts.

This invention may be illustrated in more detail by the following examples but it is not limited by the examples.

EXAMPLE 1

To 36 g of $Fe(NO_3)_3 \cdot 9H_2O$, 1.25 g of $Cu(NO_3)_2 \cdot 3H_2O$ and 3 g of $K_2CO_3$ dissolved in 100 g of water was added 20 g of $\gamma$—$Al_2O_3$. The mixture was vigorously stirred and heated to evaporate water. After the evaporation of water, the reaction mixture was dried at 120° C. for 24 hours and calcinated at 450° C. for 6 hours. To reduce 0.5 g of calcination-completed Fe—Cu—K/$\gamma$—$Al_2O_3$ catalyst in a flow-type reactor hydrogen was flowed at 450° C. and 60 ml/g-cat./min for 24 hours. To activate the catalyst the mixture of carbon dioxide and hydrogen ($H_2/CO_2$=3 v/v) was flowed at 300° C., 10 atm and 32 ml/g-cat./min for 16 hours, and then nitrogen was flowed at 200° C., 1 atm and 20 ml/g-cat./min for 1 hour.

The mixture gas of carbon dioxide and hydrogen ($H_2/CO_2$=3 v/v) was flowed into the pretreated Fe—Cu—K/$\gamma$—$Al_2O_3$ catalyst at 300° C., 10 atm and 1800 $h^{-1}$ of the space velocity to give hydrocarbons.

The results are given in the following table. 1.

EXAMPLE 2

To 36 g of $Fe(NO_3)_3 \cdot 9H_2O$, 1.5 g of $Cu(NO_3)_2 \cdot 3H_2O$ and 0.9 g of $K_2CO$ dissolved in 100 g of water was added 20 g of $\gamma$—$Al_2O_3$. The mixture was vigorously stirred and heated to evaporate water. After the evaporation of water, the reaction mixture was dried at 120° C. for 24 hours and calcinated at 450° C. for 6 hours. To reduce 0.5 g of calcination-completed Fe—Cu—K/$\gamma$—$Al_2O_3$ catalyst in a flow-type reactor hydrogen was flowed at 450° C. and 60 ml/g-cat./min for 24 hours. To activate the catalyst the mixture of carbon dioxide and hydrogen ($H_2CO_2$=3 v/v) was flowed at 300° C., 10 atm and 32 ml/g-cat./min for 16 hours, and then nitrogen was flowed at 200° C., 1 atm and 20 ml/g-cat./min for 1 hour.

The mixture gas of carbon dioxide and hydrogen ($H_2/CO_2$=3 v/v) was flowed into the pretreated Fe—Cu—K/$\gamma$—$Al_2O_3$ catalyst at 300° C., 10 atm and 1800 $h^{-1}$ of the space velocity for 6 hours to give hydrocarbons.

The results are given in the following table 1.

COMPARATIVE EXAMPLE 1

The catalyst was prepared by the procedure of Example 1 without using $Cu(NO_3)_2 \cdot 3H_2O$ instead of 1.25 g of $Cu(NO_3)_2 \cdot 3H_2O$.

The results are given in the following table 1.

COMPARATIVE EXAMPLE 2

The catalyst was prepared by the procedure of Example 1 by using 0.8 g $Cu(NO_3)_2 \cdot 3H_2O$ instead of 1.25 g of $Cu(NO_3)_2 \cdot 3H_2O$.

The results of activity after 100 hours are given in the following table 1.

COMPARATIVE EXAMPLE 3

The catalyst was prepared by the procedure of Example 1 by using 9 g of $Cu(NO_3)_2 \cdot 3H_2O$ instead of 1.25 g of $Cu(NO_3)_2 \cdot 3H_2O$.

The results of activity after 100 hours are given in the following table 1.

COMPARATIVE EXAMPLE 4

The catalyst was prepared by the procedure of Example 1 by using silica ($SiO_2$) instead of $\gamma$-alumina ($Al_2O_3$).

The results of activity after 100 hours are given in the following table 1.

COMPARATIVE EXAMPLE 5

The catalyst was prepared by the procedure of Example 1 by using 0.3 g of $K_2CO_3$ instead of 3 g of $K_2CO_3$.

The results of activity after 100 hours are given in the following table 1.

COMPARATIVE EXAMPLE 6

The catalyst was prepared by the procedure of Example 1 excluding activation step of flowing the mixture gas of carbon dioxide and hydrogen.

The results of activity after 100 hours are given in the following table 1.

TABLE 1

| Examples | Reaction time | Conversion rate (%) | Yield (C %) Hydrocarbons | $C_1$ | $C_{2+}$ |
|---|---|---|---|---|---|
| Example 1 | 6 | 40.1 | 36.4 | 3.6 | 32.8 |
|  | 100 | 40.9 | 37.3 | 5.7 | 31.6 |
|  | 1000 | 40.5 | 37.0 | 5.5 | 31.5 |
|  | 2005 | 38.3 | 34.6 | 5.9 | 28.7 |
| Example 2 | 6 | 33.6 | 27.3 | 9.2 | 18.1 |
|  | 100 | 32.6 | 25.9 | 9.2 | 16.7 |
|  | 1000 | 32.5 | 25.6 | 8.2 | 17.4 |
|  | 2005 | 30.7 | 23.4 | 8.4 | 15.0 |
| Comp. Example 1 | 100 | 31.3 | 24.3 | 2.6 | 21.7 |
|  | 850 | 26.4 | 16.0 | 2.3 | 13.7 |
| Comp. Example 2 | 100 | 32.8 | 25.6 | 3.5 | 22.1 |
| Comp. Example 3 | 100 | 20.8 | 8.5 | 5.1 | 3.4 |
| Comp. Example 4 | 100 | 15.7 | 6.3 | 0.9 | 5.4 |
| Comp. Example 5 | 100 | 31.5 | 25.2 | 10.2 | 15.0 |
| Comp. Example 6 | 100 | 29.7 | 23.0 | 2.3 | 20.7 |

As shown in table 1, the Fe—Cu—K/γ—$Al_2O_3$ catalyst keeps its activity even after 2000 hours to produce hydrocarbons from carbon dioxide in high yield.

What is claimed is:

1. A process for preparing hydrocarbons by hydrogenation of carbon dioxide performed by flowing a gas mixture ($H_2/CO_2$=1.0~5.0 v/v) into the reactor at 200~500° C., 1~100 atm and 500~20,000 $h^{-1}$ of the space velocity over a catalyst, wherein said catalyst is a pretreated Fe—Cu—K/γ—$Al_2O_3$ by reduction and activation, including 5~50 wt. % of Fe to total catalyst weight and containing 0.07~1 of weight ratio of K/Fe and 0.05~0.5 of weight ratio of Cu/Fe, wherein said activation is performed by flowing a gas mixture ($H_2CO_2$=0.2~10 v/v) on Fe—Cu—K/γ—$Al_2O_3$ at 200~400° C., 10~40 atm and 2~200 ml/g-cat./min of the flow rate and then flowing a gas selected from the group consisting of nitrogen, argon, and helium on said Fe—Cu—K/γ—$Al_2O_3$ at 100~400° C., 1~10 atm, and 10~100 ml/g-cat./min of the flow rate.

2. The process according to claim 1, wherein said reduction is performed by flowing hydrogen on said Fe—Cu—K/γ—$Al_2O_3$ at 300~500° C., 1~10 atm, and 20~100 ml/g-cat./min of the flow rate.

* * * * *